United States Patent
Vassiliou et al.

(10) Patent No.: US 6,326,455 B2
(45) Date of Patent: Dec. 4, 2001

(54) METHODS FOR TREATING COBALT CATALYST IN OXIDATION MIXTURES RESULTING FROM OXIDATION OF HYDROCARBONS TO DIBASIC ACIDS

(75) Inventors: Eustathios Vassiliou, Newark, DE (US); Mark W. Dassel, Indianola, WA (US); Ader M. Rostami; Douglas J. Dudgeon, both of Bainbridge Island, WA (US); David C. DeCoster, Buckley, WA (US)

(73) Assignee: RPC Inc., Atlanta, GA (US)

( * ) Notice: Subject to any disclaimer, the term of this patent is extended or adjusted under 35 U.S.C. 154(b) by 0 days.

(21) Appl. No.: 09/827,656

(22) Filed: Apr. 5, 2001

Related U.S. Application Data

(62) Division of application No. 09/245,157, filed on Feb. 4, 1999, now Pat. No. 6,232,495
(60) Provisional application No. 60/074,068, filed on Feb. 9, 1998.

(51) Int. Cl.[7] ............ C08G 63/02; C07C 51/31; B01J 20/34
(52) U.S. Cl. .......... 528/272; 528/332; 528/335; 562/512.2; 562/518; 562/519; 562/521; 562/522; 562/523; 526/68; 526/69; 526/70
(58) Field of Search .................. 528/272, 332, 528/335; 562/512.2, 518, 519, 521, 522, 523; 526/68, 69, 70

(56) References Cited

U.S. PATENT DOCUMENTS

| | | |
|---|---|---|
| 1,121,532 | 12/1914 | Newberry . |
| 2,014,044 | 9/1935 | Haswell .................. 75/17 |
| 2,223,493 | 12/1940 | Loder .................. 260/537 |

(List continued on next page.)

FOREIGN PATENT DOCUMENTS

| | | |
|---|---|---|
| 4426132 A1 | 1/1996 | (DE) . |
| 4427474 A1 | 2/1996 | (DE) . |
| 439 007 A2 | 7/1991 | (EP) . |

(List continued on next page.)

OTHER PUBLICATIONS

Derwent Abstr. No. 75–79578W, for Japanese Patent JP 700116416, May 11, 1975.

Sorribes et al., "Formación de neuvas fases en el proceso de obtención de ácido adípico: causas y efectos que provocan," *Rev. R. Acad. Cienc. Exactas, Fis. Nat. Madrid* (1987), 81(1), 233–5 (+ English language translation).

*Primary Examiner*—Samuel A. Acquah
(74) *Attorney, Agent, or Firm*—Seed Intellectual Property Law Group PLLC

(57) ABSTRACT

This invention relates to methods and reactor devices for controlling the oxidation of hydrocarbons to dibasic acids, in the presence of a cobalt catalyst and a monobasic acid, such as acetic acid, by treating the catalyst from the reaction mixture, outside the oxidation zone, after the oxidation has taken place at least partially. In one preferred embodiment, the catalyst is reduced to contain, preferably predominantly and more preferably substantially, cobalt ions in valence II, and at least partially precipitated by de-watering and/or thermal treatment. In a different preferred embodiment, the catalyst in the reaction mixture is first oxidized or maintained, preferably predominantly and more preferably substantially, at valence III, the reaction mixture is de-watered, the catalyst is reduced preferably predominantly and more preferably substantially, to valence II, causing precipitation either spontaneously at a predetermined temperature or after further thermal treatment. The precipitated catalyst is preferably recycled directly or indirectly.

72 Claims, 2 Drawing Sheets

U.S. PATENT DOCUMENTS

| | | | |
|---|---|---|---|
| 2,223,494 | 12/1940 | Loder | 260/586 |
| 2,301,240 | 11/1942 | Baumann et al. | 183/115 |
| 2,439,513 | 4/1948 | Hamblet et al. | 260/533 |
| 2,557,282 | 6/1951 | Hamblet et al. | 260/533 |
| 2,565,087 | 8/1951 | Porter et al. | 260/631 |
| 2,980,523 | 4/1961 | Dille et al. | 48/215 |
| 3,161,603 | 12/1964 | Leyshon et al. | 252/413 |
| 3,231,608 | 1/1966 | Kollar | 260/533 |
| 3,234,271 | 2/1966 | Barker et al. | 260/431 |
| 3,290,369 | 12/1966 | Bonfield et al. | 260/537 |
| 3,361,806 | 1/1968 | Lidov | 260/531 |
| 3,515,751 | 6/1970 | Oberster et al. | 260/533 |
| 3,530,185 | 9/1970 | Pugi | 260/586 |
| 3,613,333 | 10/1971 | Gardenier | 55/89 |
| 3,677,696 | 7/1972 | Bryk et al. | 23/2 |
| 3,839,435 | 10/1974 | Shigeyasu et al. | 260/524 R |
| 3,928,005 | 12/1975 | Laslo | 55/73 |
| 3,932,513 | 1/1976 | Russell | 260/586 |
| 3,946,076 | 3/1976 | Paasen et al. | 260/586 |
| 3,957,876 | 5/1976 | Rapoport et al. | 260/586 |
| 3,987,100 | 10/1976 | Barnette et al. | 260/586 |
| 3,987,808 | 10/1976 | Carbonell et al. | 137/3 |
| 4,025,498 | 5/1977 | Buss et al. | 260/95 A |
| 4,032,569 | 6/1977 | Onopchenko et al. | 260/533 C |
| 4,039,304 | 8/1977 | Bechthold et al. | 55/10 |
| 4,055,600 | 10/1977 | Langley et al. | 260/586 |
| 4,065,527 | 12/1977 | Graber | 261/79 A |
| 4,158,739 | 6/1979 | Schulz et al. | 562/543 |
| 4,160,108 | 7/1979 | Shigeyasu et al. | 562/416 |
| 4,263,453 | 4/1981 | Schulz et al. | 562/543 |
| 4,308,037 | 12/1981 | Meissner et al. | 55/10 |
| 4,332,590 | 6/1982 | Smith | 23/230 A |
| 4,361,965 | 12/1982 | Goumondy et al. | 34/57 R |
| 4,370,304 | 1/1983 | Hendriks et al. | 422/224 |
| 4,394,139 | 7/1983 | Board | 55/20 |
| 4,419,184 | 12/1983 | Backlund | 162/49 |
| 4,423,018 | 12/1983 | Lester, Jr. et al. | 423/243 |
| 4,477,380 | 10/1984 | Knips et al. | 260/385 |
| 4,603,220 | 7/1986 | Feld | 562/416 |
| 5,061,453 | 10/1991 | Krippl et al. | 422/106 |
| 5,104,492 | 4/1992 | King et al. | 203/15 |
| 5,123,936 | 6/1992 | Stone et al. | 55/8 |
| 5,170,727 | 12/1992 | Nielsen | 110/346 |
| 5,221,800 | 6/1993 | Park et al. | 562/543 |
| 5,244,603 | 9/1993 | Davis | 261/87 |
| 5,270,019 | 12/1993 | Melton et al. | 422/234 |
| 5,271,904 | 12/1993 | Esposito et al. | 422/105 |
| 5,286,458 | 2/1994 | Yang et al. | 422/168 |
| 5,294,378 | 3/1994 | Succi et al. | 261/130 |
| 5,312,567 | 5/1994 | Kozma et al. | 261/87 |
| 5,321,157 | 6/1994 | Kollar | 562/543 |
| 5,374,767 | 12/1994 | Drinkard et al. | 560/193 |
| 5,396,850 | 3/1995 | Conochie et al. | 110/346 |
| 5,399,750 | 3/1995 | Brun et al. | 562/553 |
| 5,463,119 | 10/1995 | Kollar | 562/543 |
| 5,502,245 | 3/1996 | Dassel et al. | 562/413 |
| 5,516,423 | 5/1996 | Conoby et al. | 210/85 |
| 5,558,842 | 9/1996 | Vassiliou et al. | 422/108 |
| 5,580,531 | 12/1996 | Vassiliou et al. | 422/108 |
| 5,654,475 | 8/1997 | Vassiliou et al. | 562/413 |
| 5,756,837 | 5/1998 | Constantini et al. | 562/543 |
| 5,801,273 | 9/1998 | Vassiliou et al. | 562/413 |
| 5,801,282 | 9/1998 | Dassel et al. | 562/413 |
| 5,817,868 | 10/1998 | Rostami et al. | 562/413 |
| 5,824,819 | 10/1998 | Dassel et al. | 562/529 |

FOREIGN PATENT DOCUMENTS

| | | |
|---|---|---|
| 729 084 A1 | 8/1996 | (EP) . |
| 729 085 A1 | 8/1996 | (EP) . |
| 751 105 A2 | 1/1997 | (EP) . |
| 2 722 783 A1 | 1/1996 | (FR) . |
| 415172 | 8/1934 | (GB) . |
| 738808 | 10/1955 | (GB) . |
| 864106 | 3/1961 | (GB) . |
| 1143213 | 2/1969 | (GB) . |
| 2014473 | 8/1979 | (GB) . |
| 48-003815 | 2/1973 | (JP) . |
| 50034006B | 11/1975 | (JP) . |
| WO 96/03365 | 2/1996 | (WO) . |
| WO 96/40610 | 12/1996 | (WO) . |
| WO 97/49485 | 12/1997 | (WO) . |

METHODS FOR TREATING COBALT CATALYST IN OXIDATION MIXTURES RESULTING FROM OXIDATION OF HYDROCARBONS TO DIBASIC ACIDS

CROSS-REFERENCE TO RELATED APPLICATIONS

This application is a divisional of pending U.S. patent application Ser. No. 09/245,157, filed Feb. 4, 1999 U.S. Pat. No. 6,232,495; which claims the priority benefit of U.S. Provisional Application No. 60/074,068, filed Feb. 9, 1998, which application is incorporated herein by reference in its entirety.

FIELD OF THE INVENTION

This invention relates to methods of oxidizing hydrocarbons, such as cyclohexane for example, to respective dibasic acids, such as adipic acid for example, and more specifically, how to treat catalyst after the reaction, preferably for recycling.

BACKGROUND OF THE INVENTION

There is a plethora of references (both patents and literature articles) dealing with the formation of acids, one of the most important being adipic acid, by oxidation of hydrocarbons. Adipic acid is used to produce Nylon 66 fibers and resins, polyesters, polyurethanes, and miscellaneous other compounds.

There are different processes of manufacturing adipic acid. The conventional process involves a first step of oxidizing cyclohexane with oxygen to a mixture of cyclohexanone and cyclohexanol (KA mixture), and then oxidation of the KA mixture with nitric acid to adipic acid. Other processes include, among others, the "Hydroperoxide Process", the "Boric Acid Process", and the "Direct Synthesis Process", which involves direct oxidation of cyclohexane to adipic acid with oxygen in the presence of solvents, catalysts, and promoters.

The Direct Synthesis Process has been given attention for a long time. However, to this date it has found little commercial success. One of the reasons is that although it looks very simple at first glance, it is extremely complex in reality. Due to this complexity, one can find strikingly conflicting results, comments, and views in different references.

It is well known that after a reaction has taken place according to the Direct Synthesis, a mixture of two liquid phases is present at ambient temperature, along with a solid phase mainly consisting of adipic acid. The two liquid phases have been called the "Polar Phase" and the "Non-Polar Phase". However, no attention has been paid so far to the importance of the two phases, except for separating the adipic acid from the "Polar Phase" and recycling these phases to the reactor partially or totally with or without further treatment.

It is also important to note that most studies on the Direct Synthesis have been conducted in a batch mode, literally or for all practical purposes.

As aforementioned, there is a plethora of references dealing with oxidation of organic compounds to produce acids, such as, for example, adipic acid and/or intermediate products, such as for example cyclohexanone, cyclohexanol, cyclohexylhydroperoxide, etc.

The following references, among others, may be considered as representative of oxidation processes relative to the preparation of diacids and other intermediate oxidation products.

U.S. Pat. No. 5,463,119 (Kollar) discloses a process for the oxidative preparation of $C_5$–$C_8$ aliphatic dibasic acids by (1) reacting,
   (a) at least one saturated cycloaliphatic hydrocarbon having from 5 to 8 ring carbon atoms in the liquid phase and
   (b) an excess of oxygen gas or an oxygen-containing gas in the presence of
   (c) a solvent comprising an organic acid containing only primary and/or secondary hydrogen atoms and
   (d) at least about 0.002 mole per 1000 grams of reaction mixture of a polyvalent heavy metal catalyst;
(2) removing the aliphatic dibasic acid; and
(3) recycling intermediates, post oxidation components, and derivatives thereof remaining after removal of the aliphatic dibasic acid into the oxidation reaction.

U.S. Pat. No. 5,374,767 (Drinkard et al.) discloses formation of cyclohexyladipates in a staged reactor, e.g., a reactive distillation column. A mixture containing a major amount of benzene and a minor amount of cyclohexene is fed to the lower portion of the reaction zone and adipic acid is fed to the upper portion of the reaction zone, cyclohexyladipates are formed and removed from the lower portion of the reaction zone and benzene is removed from the upper portion of the reaction zone. The reaction zone also contains an acid catalyst.

U.S. Pat. No. 5,321,157 (Kollar) discloses a process for the preparation of $C_5$–$C_8$ aliphatic dibasic acids through oxidation of corresponding saturated cycloaliphatic hydrocarbons by (1) reacting, at a cycloaliphatic hydrocarbon conversion level of between about 7% and about 30%,
   (a) at least one saturated cycloaliphatic hydrocarbon having from 5 to 8 ring carbon atoms in the liquid phase and
   (b) an excess of oxygen gas or an oxygen containing gas mixture in the presence of
   (c) less than 1.5 moles of a solvent per mole of cycloaliphatic hydrocarbon (a), wherein said solvent comprises an organic acid containing only primary and/or secondary hydrogen atoms and
   (d) at least about 0.002 mole per 1000 grams of reaction mixture of a polyvalent heavy metal catalyst; and
(2) isolating the C5–C8 aliphatic dibasic acid.

U.S. Pat. No. 3,987,100 (Barnette et al.) describes a process of oxidizing cyclohexane to produce cyclohexanone and cyclohexanol, said process comprising contacting a stream of liquid cyclohexane with oxygen in each of at least three successive oxidation stages by introducing into each stage a mixture of gases comprising molecular oxygen and an inert gas.

U.S. Pat. No. 3,957,876 (Rapoport et al.) describes a process for the preparation of cyclohexyl hydroperoxide substantially free of other peroxides by oxidation of cyclohexane containing a cyclohexane soluble cobalt salt in a zoned oxidation process in which an oxygen containing gas is fed to each zone in the oxidation section in an amount in excess of that which will react under the conditions of that zone.

U.S. Pat. No. 3,932,513 (Russell) discloses the oxidation of cyclohexane with molecular oxygen in a series of reaction zones, with vaporization of cyclohexane from the last reactor effluent and parallel distribution of this cyclohexane vapor among the series of reaction zones.

U.S. Pat. No. 3,530,185 (Pugi) discloses a process for manufacturing precursors of adipic acid by oxidation with an oxygen-containing inert gas which process is conducted in at least three successive oxidation stages by passing a stream of liquid cyclohexane maintained at a temperature in the range of 140° to 200° C. and a pressure in the range of 50 to 350 p.s.i.g. through each successive oxidation stage and by introducing a mixture of gases containing oxygen in each oxidation stage in an amount such that substantially all of the oxygen introduced into each stage is consumed in that stage thereafter causing the residual inert gases to pass countercurrent into the stream of liquid during the passage of the stream through said stages.

U.S. Pat. No. 3,515,751 (Oberster et al.) discloses a process for the production of epsilon-hydroxycaproic acid in which cyclohexane is oxidized by liquid phase air oxidation in the presence of a catalytic amount of a lower aliphatic carboxylic acid and a catalytic amount of a peroxide under certain reaction conditions so that most of the oxidation products are found in a second, heavy liquid layer, and are directed to the production of epsilon-hydroxycaproic acid.

U.S. Pat. No. 3,361,806 (Lidov et al.) discloses a process for the production of adipic acid by the further oxidation of the products of oxidation of cyclohexane after separation of cyclohexane from the oxidation mixture, and more particularly to stage wise oxidation of the cyclohexane to give high yields of adipic acid precursors and also to provide a low enough concentration of oxygen in the vent gas so that the latter is not a combustible mixture.

U.S. Pat. No. 3,234,271 (Barker et al.) discloses a process for the production of adipic acid by the two-step oxidation of cyclohexane with oxygen. In a preferred embodiment, mixtures comprising cyclohexanone and cyclohexanol are oxidized. In another embodiment, the process involves the production of adipic acid from cyclohexane by oxidation thereof, separation of cyclohexane from the oxidation mixture and recycle thereof, and further oxidation of the other products of oxidation.

U.S. Pat. No. 3,231,608 (Kollar) discloses a process for the preparation of aliphatic dibasic acids from saturated cyclic hydrocarbons having from 4 to 8 cyclic carbon atoms per molecule in the presence of a solvent which comprises an aliphatic monobasic acid which contains only primary and secondary hydrogen atoms and a catalyst comprising a cobalt salt of an organic acid, and in which process the molar ratio of said solvent to said saturated cyclic hydrocarbon is between 1.5:1 and 7:1, and in which process the molar ratio of said catalyst to said saturated cyclic hydrocarbon is at least 5 millimoles per mole.

U.S. Pat. No. 3,161,603 (Leyshon et al.) discloses a process for recovering the copper-vanadium catalyst from the waste liquors obtained in the manufacture of adipic acid by the nitric acid oxidation of cyclohexanol and/or cyclohexanone.

U.S. Pat. No. 2,565,087 (Porter et al.) discloses the oxidation of cycloaliphatic hydrocarbons in the liquid phase with a gas containing molecular oxygen and in the presence of about 10% water to produce two phases and avoid formation of esters.

U.S. Pat. No. 2,557,282 (Hamblet et al.) discloses production of adipic acid and related aliphatic dibasic acids; more particularly to the production of adipic acid by the direct oxidation of cyclohexane.

U.S. Pat. No. 2,439,513 (Hamblet et al.) discloses the production of adipic acid and related aliphatic dibasic acids and more particularly to the production of adipic acid by the oxidation of cyclohexane.

U.S. Pat. No. 2,223,494 (Loder et al.) discloses the oxidation of cyclic saturated hydrocarbons and more particularly to the production of cyclic alcohols and cyclic ketones by oxidation of cyclic saturated hydrocarbons with an oxygen-containing gas.

U.S. Pat. No. 2,223,493 (Loder et al.) discloses the production of aliphatic dibasic acids and more particularly to the production of aliphatic dibasic acids by oxidation of cyclic saturated hydrocarbons with an oxygen-containing gas.

German Patent DE 44 26 132 A1 (Kysela et al.) discloses a method of dehydration of process acetic acid from liquid-phase oxidation of cyclohexane with air, in the presence of cobalt salts as a catalyst after separation of the adipic acid after filtration, while simultaneously avoiding cobalt salt precipitates in the dehydration column, characterized in that the acetic acid phase to be returned to the beginning of the process is subjected to azeotropic distillation by the use of added cyclohexane, under distillative removal of the water down to a residual content of less than [sic] 0.3–0.7%.

PCT International Publication WO 96/03365 (Constantini et al.) discloses a process for recycling a cobalt-containing catalyst in a direct reaction of oxidation of cyclohexane into adipic acid, characterized by including a step in which the reaction mixture obtained by oxidation into adipic acid is treated by extraction of at least a portion of the glutaric acid and the succinic acid formed during the reaction.

U.S. Pat. No. 5,221,800 (Park et al.) discloses a process for the manufacture of adipic acid. In this process, cyclohexane is oxidized in an aliphatic monobasic acid solvent in the presence of a soluble cobalt salt wherein water is continuously or intermittently added to the reaction system after the initiation of oxidation of cyclohexane as indicated by a suitable means of detection, and wherein the reaction is conducted at a temperature of about 50° C. to about 150° C. at an oxygen partial pressure of about 50 to 420 pounds per square inch absolute.

U.S. Pat. No. 4,263,453 (Schultz et al.) discloses a process claiming improved yields by the addition of water at the beginning of the reaction, generally of the order of 0.5 to 15% relative to monobasic aliphatic acid solvent, and preferably 1 to 10% relative to the solvent.

U.S. Pat. No. 3,390,174 (Schultz et al.) discloses a process claiming improved yields of aliphatic dibasic acids when oxidizing the respective cyclic hydrocarbons at temperatures between 130° and 160° C., while removing the water of reaction substantially as quickly as it is formed.

None of the above references, or any other references known to the inventors disclose, suggest or imply, singly or in combination, treatment of catalyst, from hydrocarbon reaction mixtures, preferably for recycling, subject to the intricate and critical controls and requirements of the instant invention as described and claimed.

Our U.S. Pat. Nos. 5,801,282; 5,580,531; 5,654,475; 5,558,842; and 5,502,245; our copending U.S. patent application Ser. No. 08/587,967 (filed Jan. 1, 1996), and PCT International publication WO 96/07056, all of which are incorporated herein by reference, describe methods and apparatuses relative to controlling reactions in atomized liquids.

Our U.S. Pat. Nos. 5,824,819; 5,817,868; and 5,801,273; and our co-pending U.S. patent application Ser. Nos. 08/812, 847 filed on Mar. 6, 1997; Ser. No. 08/824,992, filed on Mar. 27, 1997; Ser. No. 08/861,180, filed on May 21, 1997; Ser. No. 08/861,281, filed on May 21, 1997; Ser. No. 08/861,210, filed on May 21, 1997; Ser. No. 08/876,692, filed on Jun. 16, 1997; Ser. No. 08/900,323, filed on Jul. 25, 1997; Ser. No. 08/931,035, filed on Sep. 16, 1997; Ser. No. 08/932,875, filed on Sep. 18, 1997; Ser. No. 08/934,253, filed on Sep. 19, 1997; Ser. No. 08/989,910, filed on Dec. 12, 1997; Ser. No. 08/986,505 filed Dec. 8, 1997; No. 60/074,068 filed Feb. 9, 1998; No. 60/075,257 filed Feb. 19, 1998; No. 60/086,159 filed May 20, 1998; No. 60/086,118 filed May 20, 1998; No. 60/101,918 filed Sep. 1998; No. 60/086,119 filed May 20, 1998; No. 60/091,483 filed Jul. 2, 1998; No. 60/093,256 filed Jul. 17, 1998; No. 60/091,796 filed Jul. 6, 1998; No. 60/105,048 filed Oct. 20, 1998; No. 60/111,848 filed Dec. 11, 1998; No. 60/110,206 filed Nov. 30, 1998; as well as concurrently filed "Methods and Devices for Separating Catalyst from Oxidation Mixtures", are all also incorporated herein by reference.

All of our following PCT patent applications, are also incorporated herein by reference: PCT/US97/10830 filed on Jun. 23, 1997 (WO 97/49485); PCT/US97/12944 filed on Jul. 23, 1997 (WO 98/07677); PCT/US96/07056 filed May 17, 1996 (WO 96/40610); PCT/US97/17684 filed Sep. 30, 1997 (WO 98/19789); PCT/US97/17812 filed Oct. 2, 1997 (WO 98/27029); PCT/US97/17883 filed Oct. 3, 1997 (WO 98/20966); PCT/US98/25105 filed Dec. 1, 1998; PCT/US98/19111 filed Sep. 14, 1998; PCT/US98/14506 filed Jul. 13, 1998; PCT/US98/19099 filed Sep. 16, 1998; and PCT/US98/19057 filed Sep. 14, 1998.

SUMMARY OF THE INVENTION

As aforementioned, this invention relates to methods of oxidizing hydrocarbons, such as cyclohexane for example, to respective intermediate oxidation products, such as adipic acid for example. More specifically, this invention relates to a method of handling catalyst containing cobalt (Co) in a reaction mixture produced by oxidation of a hydrocarbon to a dibasic acid, the reaction mixture containing the catalyst and a monobasic acid solvent, the method being characterized by one of two steps:

either a step of reducing the Co to or maintaining the Co predominantly or substantially at valence II {Co(II)} if proximate de-watering and/or thermal precipitation is desired;

or a step of oxidizing the Co to or maintaining the Co predominantly or substantially at valence III {Co(III)} if proximate de-watering and/or thermal precipitation is to be avoided.

The Co may be reduced to or maintained, predominantly or substantially, at valence II, and the mixture may then be de-watered and/or thermally treated, so as to cause catalyst precipitation. The step of catalyst precipitation may be followed directly or indirectly by a step of oxidizing the Co to, predominantly or substantially, valence III, and/or a step of storing any mixture containing the catalyst.

Also, the Co may be oxidized or maintained predominantly or substantially at valence III, and the method may further comprise a step of de-watering the reaction mixture, while the Co is predominantly or substantially at valence III, and a separate step of reducing the Co to valence II, thus causing spontaneous catalyst precipitation at a predetermined temperature or precipitation after further thermal treatment. The de-watering step is preferably conducted in a dehydration column, and the step of reducing the Co to valence II is preferably conducted outside the dehydration column.

Any step of catalyst precipitation may be followed directly or indirectly by a step of oxidizing the Co to predominantly or substantially valence III, and/or a step of storing and/or recycling any mixture containing the catalyst.

It is preferable that any steps of reducing or oxidizing the Co are preceded by a step of at least partially removing the dibasic acid.

Preferably, the hydrocarbon comprises a compound selected from a group consisting of cyclohexane, cyclohexanone, cyclohexanol, cyclohexylhydroperoxide, and a mixture thereof, the monobasic acid solvent comprises acetic acid, and the dibasic acid comprises adipic acid. The methods of this invention are particularly applicable in the case that the hydrocarbon comprises cyclohexane, the solvent comprises acetic acid, and the dibasic acid comprises adipic acid.

The methods of this invention may further comprise a step of reacting the adipic acid with a reactant selected from a group consisting of a polyol, a polyamine, and a polyamide in a manner to form a polymer of a polyester, or a polyamide, or a polyimide and/or polyamideimide. The methods may further comprise a step of spinning the polymer into fibers.

Predominant oxidation of Co(II) to Co(III) means that more than 50% by weight of the cobalt ion in the oxidized matter is in the form of Co(III). Similarly, predominant reduction of Co(III) to Co(II) means that more than 50% by weight of the cobalt ion in the reduced matter is in the form of Co(II).

"Substantially" means "for all practical purposes".

All ratios and percentages are expressed by weight unless otherwise specified.

The meaning of "de-watering" and "dehydration" is the same and corresponds to partial or total removal of water, unless otherwise indicated.

A controller, preferably a computerized controller, may handle with ease and accuracy the operation of the devices of the present invention. Programming a computerized controller to perform such functions is a routine process, well known to the art. According to this invention, a controller, based on information received, from a reaction or oxidation zone for example, controls feed rates, temperatures, pressures, and other parameters in order to achieve the desirable results. The controller may also be programmed, by techniques well known to the art, to include flow sheet simulation, which may account for vapor/liquid equilibrium and energy balance effects.

As aforementioned, these methods and devices are particularly suited in case that the hydrocarbon comprises cyclohexane, the mixture comprises acetic acid, and the catalyst comprises a cobalt salt.

BRIEF DESCRIPTION OF THE DRAWINGS

The reader's understanding of this invention will be enhanced by reference to the following detailed description taken in combination with the drawing figure, wherein.

DETAILED DESCRIPTION OF THE INVENTION

As aforementioned, this invention relates to methods and devices for oxidizing hydrocarbons, such as cyclohexane for example, to respective dibasic acids, such as adipic acid for example, and more specifically, how to recover Co catalyst, preferably for recycling.

It was found by the inventors in the past that very important factors regarding partial catalyst precipitation in a reaction mixture are water level, catalyst level, hydrocarbon level, and temperature, among others, which include reaction products and by-products. For a given set of factors, partial catalyst precipitation is facilitated as the water level decreases, the catalyst level increases, the hydrocarbon level increases, and as temperature increases.

De-watering or dehydration is preferably conducted by use of distillation columns and/or addition of anhydrides, preferably acetic acid anhydride. However, other methods, such as for example use of other de-watering compounds, are not excluded and may be used very effectively, especially in combination with distillation columns. Examples of other de-watering compounds are colloidal silica, calcium oxide, molecular sieves, etc.

More recently, the inventors discovered that for Co catalyst to precipitate by de-watering and/or thermal treatment, the Co has to be at least predominantly, in valence state II. Co at valence state III does not precipitate under practical conditions in the reaction mixture before or after at least partial removal of dibasic acid.

For better clarification of this invention, the examples given below assume that the hydrocarbon comprises cyclohexane, the intermediate oxidation product comprises adipic acid, the mixture contains a solvent comprising acetic acid, and the catalyst comprises a cobalt compound. It should be understood, however, that the teachings of this invention are applicable to different hydrocarbons, intermediate oxidation products, solvents, and catalysts than the ones used in the examples. Only minor modifications may be needed to fit each individual case.

Figure 1:
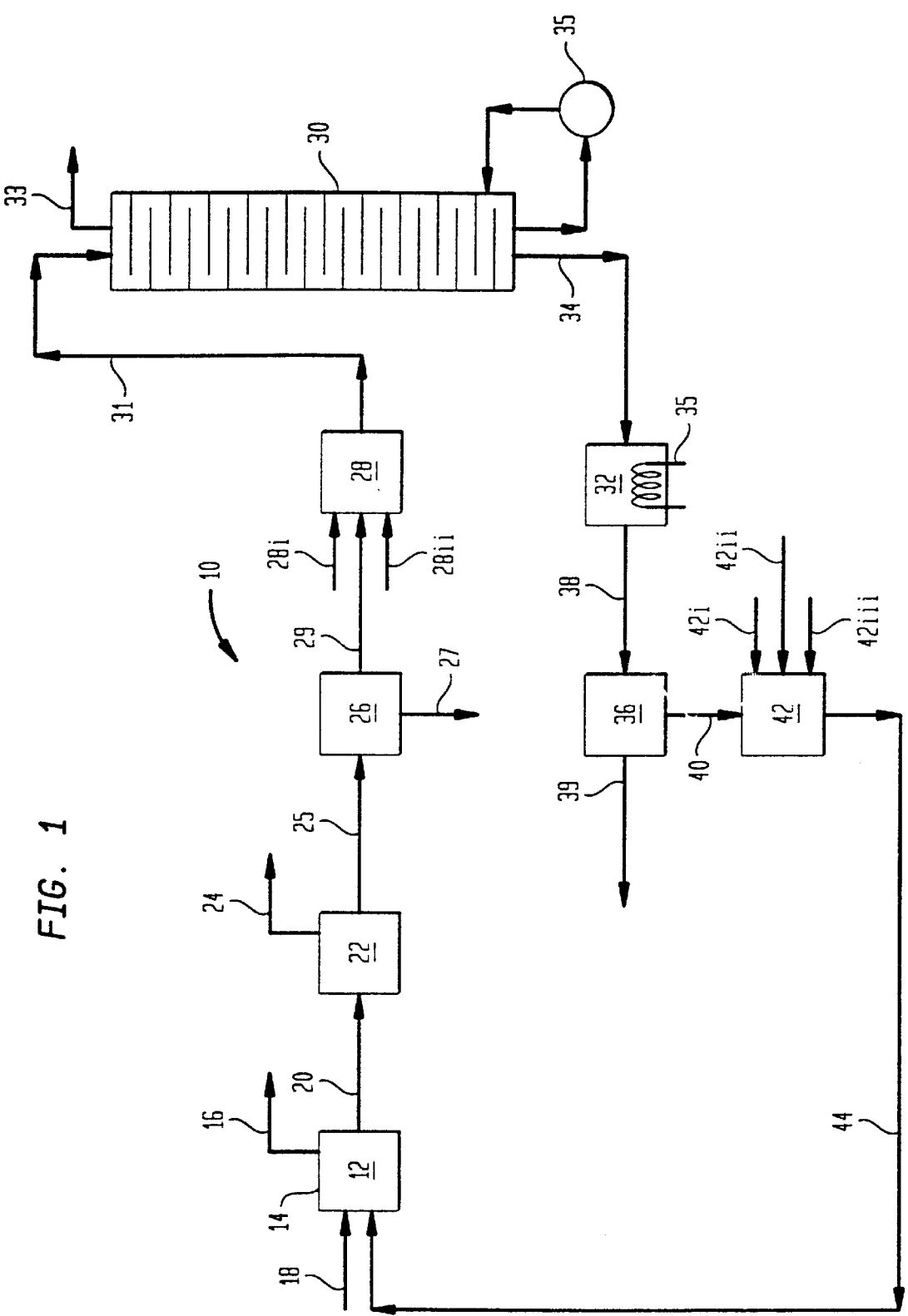
FIG. 1 illustrates a block diagram of a preferred embodiment of the present invention, wherein, after an oxidation of a hydrocarbon to form a dibasic acid in the presence of Co catalyst, the Co is reduced or maintained, predominantly or substantially, to valence II, and precipitated by de-watering and/or thermal treatment.

Referring now to FIG. 1, there is depicted a reactor device or system 10, comprising an oxidation chamber 12 containing an oxidation zone 14. The reactor device 10 is only partially shown for demonstrating the components necessary to exemplify the present invention. Miscellaneous treatment, product or by-product separation, recycling, etc. devices, well known to the art, are not shown for purposes of clarity and brevity. Also devices connected to the oxidation reactor 12, such as for example distillation columns, condensers, re-boilers, etc., are not shown, also for purposes of brevity and clarity, and they are represented in this particular example by oxidation chamber exit line 16. The oxidation reactor 12 may be any type of reactor, such as for example stirred tank reactor, atomization reactor, recirculation reactor, etc.

Feeding means (for raw materials, miscellaneous recycled matter, gaseous oxidant, etc.) connected to the oxidation chamber 12 are represented by a single feeding line 18 for purposes of clarity and brevity. However, it should be understood that, in practice, a number of individual lines may be used, including if appropriate, devices such as for example mixing vessels, heaters, coolers, etc.

The oxidation chamber 12 is connected (through transfer line 20) to a dibasic acid precipitation station 22, which is preferably a flash crystallizer, in turn connected to a flash line 24, through which flash line, the pressure is relieved to a lower pressure, preferably atmospheric, and more preferably sub-atmospheric, thus reducing the temperature in the precipitation station 22 and causing crystallization of crystallizable matter. The dibasic acid precipitation station 22 may be a single-stage or multi-stage flash crystallizer, where the pressure and temperature are reduced consecutively in the different stages. For example, if it is a two stage flash crystallizer (not shown), the pressure may be reduced to atmospheric in the first stage and to sub-atmospheric in the second stage. Additional cooling may be achieved in many ways, including utilization of coolers (not shown), and other methods or devices. Such flash crystallizers are described in detail, for example, in our copending U.S. application Ser. No. 08/824,992, filed Mar. 27, 1997.

The dibasic acid precipitation station 22 is also connected to a dibasic acid separator 26 (through a transfer line 25), which is suited to separate liquids from solids. Examples of separators are centrifugal separators and filtering devices, such as filter-presses for example, among others, very well known to the art. The dibasic acid separator 26 is connected to dibasic acids removal line 27. The separator 26 is also connected to a catalyst reducing station 28 through a first mother liquor line 29. The catalyst reducing station 28 is preferably provided with (a) a feeding line 28$i$, through which a reducing agent may be introduced to the station 28 for the purpose of reducing any Co (III) present to Co (II), and (b) an inert gas line 28$ii$ for removing oxygen and providing an inert atmosphere in the station 28, which may be a heated vessel or a non-heated vessel.

The dibasic acid precipitation station 22 and the separator 26 are not necessary for the practice of this invention, but their presence between the oxidation chamber 12 and the catalyst reducing station 28 is preferable.

The catalyst reducing station 28 is in turn connected to a de-watering station 30 through transfer line 31. The de-watering station 30 leads to a thermal treatment station 32 through transfer line 34. The thermal treatment station 32 is preferably provided with a heater 35. The de-watering station 30 may be in the form of a distillation column 30, which column 30 is provided with an exit line 33, while the thermal treatment station 32 may be in the form of a heated tank. The de-watering station 30, if in the form of a column, is also preferably provided with re-boiler 35, unless a different source to drive the column is provided.

Agitation (not shown) may be provided in the different station, such as stations 28 and 32, for example.

It should be pointed out that the de-watering station and the thermal treatment station may be just one unit, and that only one of the two stations may be required depending on the circumstances. If the water level of the contents of catalyst reducing station 28, for example, is low enough, heating the reaction mixture to a higher temperature in the thermal treatment station 32 (even in the absence of the de-watering station 30) may be adequate to cause precipitation of catalyst to a required degree. Similarly, if the temperature at the lower part of a distillation column is adequately high and the water level adequately low, precipitation of catalyst may occur. Further, addition of an anhydride, such as acetic acid anhydride for example, added to the de-watering station 30, or directly to the thermal treatment station 32, can lower the water level so that catalyst precipitates at the prevailing temperature inside the station 32. Our U.S. patent application Ser. No. 08/931,035, filed Sep. 16, 1997, gives a plurality of examples of such devices which may be used for catalyst precipitation.

The thermal treatment station 32 is connected to a catalyst separator 36 through transfer line 38. The catalyst separator 36 is provided with a catalyst removal line 40, which may be directly connected to the oxidation chamber 12. However, the catalyst removal line 40 may also be connected to a re-dissolving and/or oxidation station 42, where the catalyst may be re-dissolved and/or the Co, preferably predominantly and more preferably substantially, oxidized to valence III. A non-gaseous oxidant addition line 42*i*, and/or a gaseous oxidant addition line 42*iii*, and/or a solvent addition line 42*ii*, may be preferably connected to the re-dissolving and/or oxidation station 42.

The catalyst separator 36 is also provided with a second mother liquor line 39, which is connected (not shown) to further treatment means (not shown), for further treatment, such as for example removal of additional catalyst, separation of dibasic acids, separation and/or treatment of by-products, etc.

The re-dissolving and/or oxidation station 42 is connected to the oxidation station 12 through catalyst recycle line 44. The re-dissolving and/or oxidation station 42 may instead be connected to a storage, if so desired.

In operation of this embodiment, raw materials are fed through line 18 to the oxidation chamber 12, which encloses the oxidation zone 14. Oxidation chambers are well known to the art. According to this invention, in the case of adipic acid manufacture by direct oxidation of cyclohexane, the raw materials are preferably cyclohexane as the hydrocarbon, acetaldehyde or cyclohexanone as the initiator, oxygen or a gas (such as an inert gas, like nitrogen for example) containing oxygen, a cobalt compound as catalyst, and acetic acid as the monobasic acid solvent. A small amount of water in the oxidation zone is preferably controlled to be higher than that at or under which catalyst precipitates, but lower than that at or over which a second liquid phase is formed. It is also preferable that the raw materials and the conditions are maintained at a steady state. By the term "steady state", it is meant that the reaction has reached an equilibrium, which equilibrium, however, may be adjusted periodically or continuously in order to achieve a desired result. If for example more water is needed in the reaction or oxidation zone to avoid catalyst precipitation, the water feed rate to the reaction or oxidation zone may be increased appropriately, and still the reaction may be considered to be at a "steady state". Similarly, if less water is needed to avoid formation of two phases, the water feed rate to the reaction or oxidation zone may be decreased appropriately, and still the reaction may be considered to be at a "steady state". The feed of the rest of the ingredients or raw materials are also managed in a similar way, whether they are newly introduced or they are products of recycling.

During operation and oxidation of the hydrocarbon, cobalt catalyst exists in both II and III valences. Cobalt in valence state II may precipitate if the water level within the oxidation chamber falls below a critical level. When Co(II) precipitation occurs, the equilibrium shifts between Co(II) and CO(III) still in solution in the oxidation chamber. More cobalt in valence II is formed, and so more cobalt precipitates, until a considerable amount of catalyst is removed from the reaction cycle as being in the form of precipitated solid phase. This mechanism is, however, a mere speculation from the part of the inventors, and it should not be construed as limiting the scope of this invention.

Although it is not necessary, as aforementioned, it is nevertheless desirable in many occasions that before any catalyst treatment, including catalyst reduction, catalyst oxidation, catalyst precipitation, etc., a major part of dibasic acids, in this example adipic acid, possibly with small amounts of glutaric and succinic acids, is removed. This is accomplished in the dibasic acid precipitation station 22, preferably by flash crystallization, which, as aforementioned, may be achieved in one or more stages, wherein both temperature and pressure are reduced. The pressure is reduced through line 24, which may lead to vacuum pumps, condensers, and other accessories well known to the art. During flash crystallization, a considerable amount of cyclohexane with smaller amounts of acetic acid and water are removed through line 24. The slurry produced by the precipitation of the adipic acid, with small amounts of glutaric and succinic acids, is transferred to the dibasic acid separator 26, where the solid dibasic acid matter is separated and leaves the system through the dibasic acid removal line 27. The removed adipic acid may then be recrystallized or otherwise treated. The most common methods of solids separation are centrifugation, filtration, or gravitational settling.

The liquid remaining after removal of the solid matter, otherwise labeled as the first mother liquor, is transferred to the catalyst reducing station 28. It comprises Co catalyst, glutaric acid, succinic acid, adipic acid, acetic acid, and smaller amounts of cyclohexane, water, and other adjuncts, such as esters and other by-products. In most occasions, the Co in the first mother liquor is present in both valences II and III. Thus, if it were to be precipitated by de-watering and/or thermal treatment, only Co being in valence II would partially precipitate. Therefore, it is highly advantageous to reduce, preferably predominantly and more preferably substantially, the cobalt from valence III to valence II for a higher degree of precipitation. This operation takes place in the catalyst reducing station 28. An inert gas is introduced to the catalyst reducing station 28 through line 28*ii*, while a reducing agent is added through line 28*i*. Since reduction of Co(III) to Co(II) is not difficult, even mild reducing agents may be used for this purpose. Such mild reducing agents are for example hydrocarbons or intermediates in the reaction mixture. Inert environment for the reduction is very important, and an inert gas, such as nitrogen for example, provides an additional assurance of reducing to of maintaining the cobalt in valence (II). This is particularly true when acetaldehyde is used as the reducing agent. While acetaldehyde causes formation of radicals under the conditions of oxidizing cyclohexane for example, which radicals promote the formation of Co(III) and the final oxidation of cyclohexane by oxygen, acetaldehyde may also be utilized as a reducing agent in an inert atmosphere to cause reduction of Co(III) to Co(II). Since acetaldehyde is oxidized to acetic acid, its use is preferable as a reduction agent because no extraneous matter is introduced to the reactor streams.

Care is taken that there is preferably an adequate amount of water present so that catalyst does not precipitate in the catalyst reducing station 28. Also, care is preferably taken so that the amount of water present is not high enough to cause formation of a second liquid phase. Preventing the formation of a second liquid phase is not usually difficult in this case, since most of the hydrocarbon (cyclohexane in this example) has already been removed (by earlier flash crystallization for example) and an abundance of solvent (acetic acid in this example) is present.

In sequence, the oxidized matter is transferred to the de-watering station 30, which is preferably a distillation column. In the distillation column, the temperature and water content are preferably kept at such levels at which no catalyst precipitation occurs. The distillation column 30 is preferably driven by re-boiler 35, if no other adequate driving force is present. It is preferable that the column operates under reduced pressure for the temperature to be maintained under the catalyst precipitation temperature at the conditions of the operation.

In turn, the de-watered (to a desired degree) matter is sent to the thermal treatment station 32, wherein the temperature is raised to such a degree that catalyst precipitates. The slurry containing the precipitated catalyst is then sent to the catalyst separator 36, where the catalyst is separated, preferably by centrifugation or filtration, or even gravitational settling. The separated catalyst may be stored, directly transferred to the oxidation chamber 12, or otherwise treated. It is preferable, as shown in FIG. 1, that it is initially sent to re-dissolving and/or oxidation station 42. At station 42, the catalyst may be simply re-dissolved in a solvent, such as for example acetic acid with or without some water (entering the station 44 through line 42ii), and then sent to the oxidation chamber 12 totally or partially through line 44, or treated and/or stored otherwise. Further, a non-gaseous oxidant, such as for example peracetic acid, hydrogen peroxide, etc. (entering through line 42i), may be used for oxidizing the Co(II) to Co(III), at least partially, before the contents of station 42 are sent to the oxidation chamber 12 totally or partially through line 44, or treated and/or stored otherwise. It is also preferable to maintain a gaseous oxidant (for example oxygen or other gas containing oxygen) atmosphere within station 42 for promoting the Co(III) valence state. Acetaldehyde and or other initiators, such as cyclohexanone, methylethylketone, etc. may be used, in the presence of preferably an oxygen atmosphere. Ozone may also be used instead of or in addition to peracetic acid and/or hydrogen peroxide and/or other oxidant.

A second mother liquor containing in this example adipic acid, glutaric acid, succinic acid, catalyst, solvent, esters, and other by-products leaves the catalyst separator 36 through line 39 for further treatment.

Figure 2:
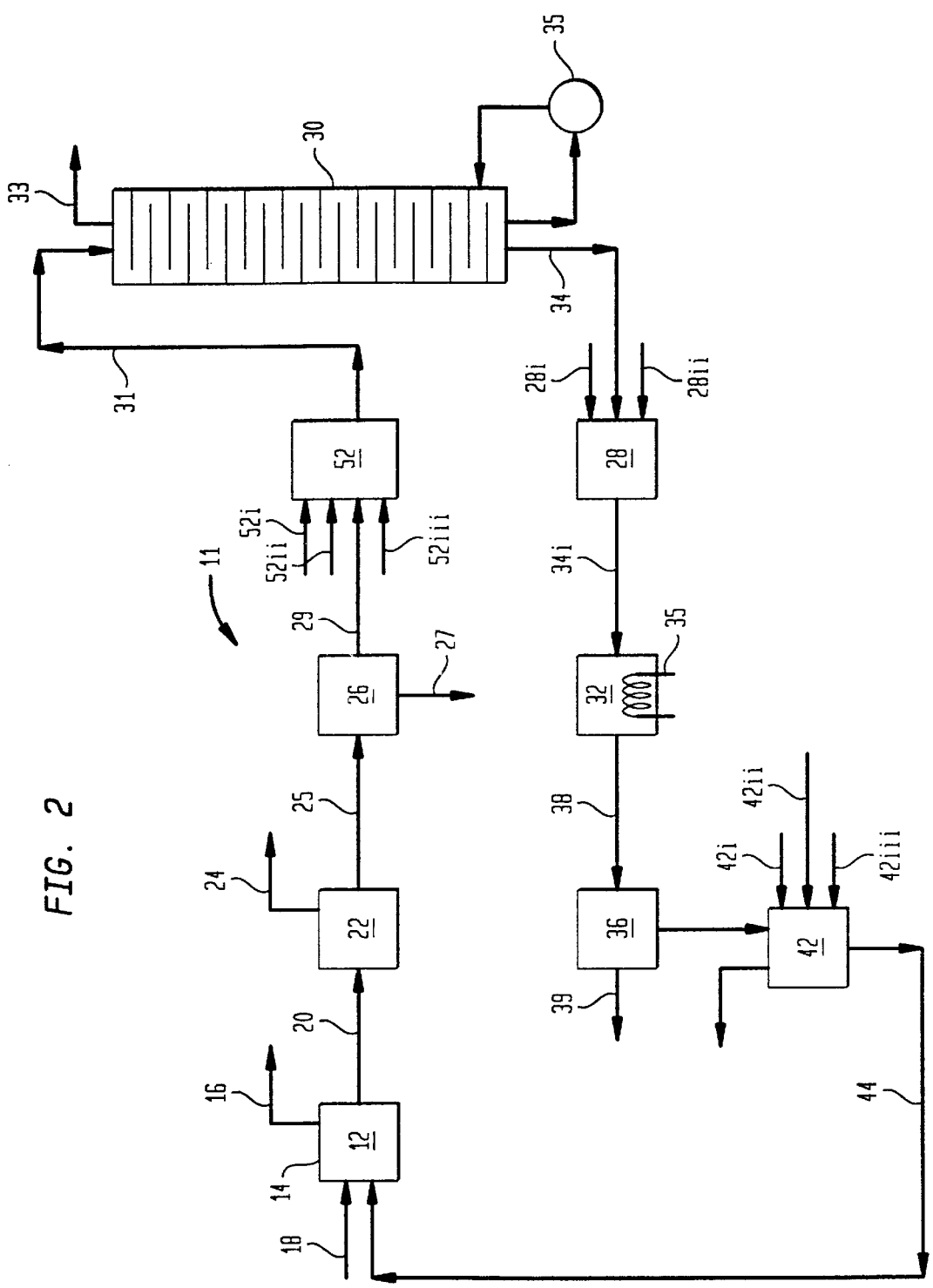
FIG. 2 illustrates a block diagram of another preferred embodiment of the present invention, wherein, after an oxidation of a hydrocarbon to form a dibasic acid in the presence of Co catalyst, the Co is oxidized or maintained, predominantly or substantially, to valence III, de-watered while being maintained, predominantly or substantially, at valence III, reduced, predominantly or substantially, to valence II, and precipitated.

Another embodiment of the present invention is illustrated in FIG. 2. The reactor system or device 11 of FIG. 2 is substantially the same as the one shown in FIG. 1 up to and including the dibasic acid separator 26. The dibasic acid separator 26 is connected to an oxidizing station 52, wherein the Co is, preferably predominantly and more preferably substantially, oxidized to valence III. A non-gaseous oxidant addition line 52i, and/or a gaseous oxidant addition line 52iii, and/or a general addition line 52ii, may be preferably connected to the oxidation station 52.

The catalyst oxidation station 52 is in turn connected, through transfer line 31, to a de-watering station 30, which is preferably a distillation column similar to the one of the previous embodiment. The de-watering station 30 leads to a catalyst reducing station 28 through line 34, which in turn is connected to a thermal treatment station 32 through transfer line 34i. In the embodiment of FIG. 2, except for the relative positioning of the miscellaneous elements, represented by the same numerals as in the embodiment of FIG. 1, the structure and function of each element is substantially identical in the two embodiments, so that no further description of these elements is necessary.

In operation of the embodiment illustrated in FIG. 2, the first mother liquor passes through the first mother liquor line 29 to the oxidation chamber 52, where the cobalt is oxidized, preferably predominately and more preferably substantially, to attain valence III. A non-gaseous oxidant, such as for example peracetic acid, hydrogen peroxide, etc. (entering through line 52i), may be used for oxidizing the Co(II) to Co(III), at least partially, before the contents of station 52 are sent to de-watering station 30 through line 31. It is also preferable to maintain a gaseous oxidant (for example oxygen or other gas containing oxygen entering through line 52iii) atmosphere within station 52 for promoting the Co(III) valence state. Use of acetaldehyde and or other initiators, such as cyclohexanone, methylethylketone, etc. may be used, in the presence of preferably an oxygen atmosphere. Such additives (or other additives including but not limited to solvent) may be introduced through the general addition line 52ii. Ozone may also be used instead of or in addition to peracetic acid and/or hydrogen peroxide and/or other oxidant.

Oxidation of Co(II) to Co(III), before the first mother liquor enters the distillation column is very important in this embodiment because this avoids and/or prevents catalyst precipitation in the column 30, even in the absence of water. Precipitation of catalyst may produce clogging of the column as well as other malfunctions. Thus, higher temperatures may be utilized in the column, and the need for a reduced pressure operation is eliminated. Reduced pressure is required for operation under the catalyst precipitation temperature in case that the cobalt is in valence II. The ability to reduce water content to very small amounts is extremely important because this is necessary for a highly efficient precipitation of catalyst in following steps.

The de-watered liquid is sent to the reducing station 28, where the Co(III) is reduced, preferably predominantly and more preferably substantially, to Co(II), in a similar manner as in the reducing station 28 of the embodiment illustrated in FIG. 1. Reduction of Co(III) to Co(II) may induce spontaneous catalyst precipitation at a predetermined temperature, at least partially, in which case the thermal treatment station 32 may be eliminated. As a matter of fact, the two stations, 28 and 32 may preferably be combined into a single unit having or lacking the heater 35. If the conditions or particular circumstances render it desirable, the stations 28 and 32 may be separate units connected by transfer line 34i. Separation and further treatment of the catalyst and a second remaining mother liquor may be conducted as described in the embodiment illustrated in FIG. 1.

In other embodiments, as aforementioned, removal of dibasic acids, such as adipic acid for example, may be performed at any a later stage.

It should be pointed out again that removal of water from a mixture includes binding the water in a manner that it is not free to act as water for the purposes of this invention. For example, partial or total reaction of an acid anhydride, such as acetic acid anhydride for example, with water contained in a mixture, is considered as water removal from the mixture, or de-watering, or dehydration, despite the fact the oxygen and hydrogen atoms, which constituted the reacted water molecule, are still present in the mixture.

It should be understood that according to the present invention, any liquids or gases or off-gases may be recycled totally or partially from any section to any other section, if so desired. Further, any combinations of the exemplifying matter, in part or in total, or any equivalent arrangements or any combinations of equivalent arrangements may be utilized, and are within the scope of the present invention.

Although miscellaneous functions are preferably controlled by a computerized controller, it is possible, according to this invention, to utilize any other type of controller or even manual controls and/or labor for controlling one or more functions. Preferred computerized controllers are artificially intelligent systems (expert systems, neural networks, and fuzzy logic systems, well known to the art). Of the three types of the artificially intelligent systems, the neural network, which is a learning system, collects information from different places of the device (for example pressure, temperature, chemical or other analysis, etc.), stores this information along with the result pressure drop rate, reaction rate, reactivity, and the like, for example), and is programmed to use this information in the future, along with other data if applicable, to make decisions regarding the action to be taken at each instance. The expert systems are programmed based on the expertise of experienced human beings. The fuzzy logic systems are based on intuition rules in addition to expertise rules.

Oxidations according to this invention, are non-destructive oxidations, wherein the oxidation product is different than carbon monoxide, carbon dioxide, and a mixture thereof, such as adipic acid for example. Of course, small amounts of these compounds may be formed along with the oxidation product, which may be one product or a mixture of products.

Examples include, but of course, are not limited to preparation of $C_5$–$C_8$ aliphatic dibasic acids from the corresponding saturated cycloaliphatic hydrocarbons, such as for example preparation of adipic acid from cyclohexane. Examples of aromatic carboxylic acids are benzoic acid, phthalic acid, isophthalic acid, and terephthalic acid, among others.

Regarding adipic acid, the preparation of which is especially suited to the methods and apparatuses of this invention, general information may be found in a plethora of U.S. Patents, among other references. These include, but are not limited to: U.S. Pat. Nos. 2,223,493; 2,589,648; 2,285,914; 3,231,608; 3,234,271; 3,361,806; 3,390,174; 3,530,185; 3,649,685; 3,657,334; 3,957,876; 3,987,100; 4,032,569; 4,105,856; 4,158,739 (glutaric acid); U.S. Pat. Nos. 4,263,453; 4,331,608; 4,606,863; 4,902,827; 5,221,800; and 5,321,157.

Dibasic acids (for example, adipic acid, phthalic acid, isophthalic acid, terephthalic acid, and the like) or other suitable compounds may be reacted, according to well known to the art techniques, with a reactant selected from a group consisting of a polyol, a polyamine, and a polyamide in a manner to form a polymer of a polyester, or a polyamide, or a polyimide and/or a polyamideimide. Preferably the polyol, the polyamine, and the polyamide are mainly a diol, a diamine, and a diamide, respectively, in order to avoid excessive cross-linking. The polymer resulting from this reaction may be spun by techniques well known to the art to form fibers.

Examples demonstrating the operation of the instant invention have been given for illustration purposes only, and should not be construed as limiting the scope of this invention in any way. In addition it should be stressed that the preferred examples discussed in detail hereinabove, as well as any other examples encompassed within the limits of the instant invention, may be practiced individually, or in any combination thereof, according to common sense and/or expert opinion. Individual sections of the examples may also be practiced individually or in combination with other individual sections of examples or examples in their totality, according to the present invention. These combinations also lie within the realm of the present invention. Furthermore, any attempted explanations in the discussion are only speculative and are not intended to narrow the limits of this invention.

What is claimed is:

1. A method of preparing a polymer, which polymer is a product of a dibasic acid with a reactant selected from a group consisting of a polyol, a polyamine, and a polyamide, the dibasic acid having been prepared by oxidizing a hydrocarbon to said polymer, the oxidizing of the hydrocarbon comprising a step of separating a Co catalyst, used for promoting oxidizing of the hydrocarbon to the dibasic acid, by a process comprising the substeps of:

(a) oxidizing substantially all Co to valence state 3 in the reaction mixture;
(b) removing substantially all water;
(c) reducing substantially all Co to valence state 2;
(d) thermally precipitating the Co to form a catalyst precipitate;
(e) separating the catalyst precipitate from the reaction mixture;
(f) forming a solution of the separated catalyst; and
(g) recycling the solution of the catalyst to any stage during or before the oxidation of the hydrocarbon.

2. A method as defined in claim 1 wherein step (a) of oxidizing the Co is preceded by a step of at least partially removing the dibasic acid.

3. A method as defined in claim 1 further comprising a step of re-oxidizing the Co substantially or predominantly to valence 3 between steps (f) and (g).

4. A method as defined in claim 2 further comprising a step of re-oxidizing the Co substantially or predominantly to valence 3 between steps (f) and (g).

5. A method as defined in claim 1 wherein the hydrocarbon comprises a compound selected from a group consisting of cyclohexane, cyclohexanone, cyclohexanol, cyclohexylhydroperoxide, and a mixture thereof, the monobasic acid solvent comprises acetic acid, and the dibasic acid comprises adipic acid.

6. A method as defined in claim 2 wherein the hydrocarbon comprises a compound selected from a group consisting of cyclohexane, cyclohexanone, cyclohexanol, cyclohexylhydroperoxide, and a mixture thereof, the monobasic acid solvent comprises acetic acid, and the dibasic acid comprises adipic acid.

7. A method as defined in claim 3 wherein the hydrocarbon comprises a compound selected from a group consisting of cyclohexane, cyclohexanone, cyclohexanol, cyclohexylhydroperoxide, and a mixture thereof, the monobasic acid solvent comprises acetic acid, and the dibasic acid comprises adipic acid.

8. A method as defined in claim 4 wherein the hydrocarbon comprises a compound selected from a group consisting of cyclohexane, cyclohexanone, cyclohexanol, cyclohexylhydroperoxide, and a mixture thereof, the monobasic acid solvent comprises acetic acid, and the dibasic acid comprises adipic acid.

9. A method as defined in claim 5 wherein the hydrocarbon comprises cyclohexane, the monobasic acid solvent comprises acetic acid, and the dibasic acid comprises adipic acid.

10. A method as defined in claim 6 wherein the hydrocarbon comprises cyclohexane, the monobasic acid solvent comprises acetic acid, and the dibasic acid comprises adipic acid.

11. A method as defined in claim 7 wherein the hydrocarbon comprises cyclohexane, the monobasic acid solvent comprises acetic acid, and the dibasic acid comprises adipic acid.

12. A method as defined in claim 8 wherein the hydrocarbon comprises cyclohexane, the monobasic acid solvent comprises acetic acid, and the dibasic acid comprises adipic acid.

13. A method as defined in claim 1 wherein the step of reducing the Co in step (c) is performed by using acetaldehyde in an inert environment.

14. A method as defined in claim 1 wherein the step of reducing the Co in step (c) is performed by using a hydrocarbon in an inert environment.

15. A method as defined in claim 1 wherein the step (a) of oxidizing the Co is induced by using acetaldehyde in an oxidative environment.

16. A method as defined in claim 2 wherein the step of reducing the Co in step (c) is performed by using acetaldehyde in an inert environment.

17. A method as defined in claim 2 wherein the step of reducing the Co in step (c) is performed by using a hydrocarbon in an inert environment.

18. A method as defined in claim 2 wherein the step (a) of oxidizing the Co is induced by using acetaldehyde in an oxidative environment.

19. A method as defined in claim 3 wherein the step of reducing the Co in step (c) is performed by using acetaldehyde in an inert environment.

20. A method as defined in claim 3 wherein the step of reducing the Co in step (c) is performed by using a hydrocarbon in an inert environment.

21. A method as defined in claim 3 wherein the step (a) of oxidizing the Co is induced by using acetaldehyde in an oxidative environment.

22. A method as defined in claim 4 wherein the step of reducing the Co in step (c) is performed by using acetaldehyde in an inert environment.

23. A method as defined in claim 4 wherein the step of reducing the Co in step (c) is performed by using a hydrocarbon in an inert environment.

24. A method as defined in claim 4 wherein the step (a) of oxidizing the Co is induced by using acetaldehyde in an oxidative environment.

25. A method of preparing a fiber by spinning a polymer, which polymer is a product of a dibasic acid with a reactant selected from a group consisting of a polyol, a polyamine, and a polyamide, the dibasic acid having been prepared by oxidizing a hydrocarbon to said polymer, the oxidizing of the hydrocarbon comprising a step of separating a Co catalyst, used for promoting oxidizing of the hydrocarbon to the dibasic acid, by a process comprising the sub-steps of:

(h) oxidizing substantially all Co to valence state 3 in the reaction mixture;

(i) removing substantially all water;

(j) reducing substantially all Co to valence state 2;

(k) thermally precipitating the Co to form a catalyst precipitate;

(l) separating the catalyst precipitate from the reaction mixture;

(m) forming a solution of the separated catalyst; and (n) recycling the solution of the catalyst to any stage during or before the oxidation of the hydrocarbon.

26. A method as defined in claim 1 wherein step (h) of oxidizing the Co is preceded by a step of at least partially removing the dibasic acid.

27. A method as defined in claim 25 further comprising a step of re-oxidizing the Co substantially or predominantly to valence 3 between steps (m) and (n).

28. A method as defined in claim 26 further comprising a step of re-oxidizing the Co substantially or predominantly to valence 3 between steps (m) and (n).

29. A method as defined in claim 25 wherein the hydrocarbon comprises a compound selected from a group consisting of cyclohexane, cyclohexanone, cyclohexanol, cyclohexylhydroperoxide, and a mixture thereof, the monobasic acid solvent comprises acetic acid, and the dibasic acid comprises adipic acid.

30. A method as defined in claim 26 wherein the hydrocarbon comprises a compound selected from a group consisting of cyclohexane, cyclohexanone, cyclohexanol, cyclohexylhydroperoxide, and a mixture thereof, the monobasic acid solvent comprises acetic acid, and the dibasic acid comprises adipic acid.

31. A method as defined in claim 27 wherein the hydrocarbon comprises a compound selected from a group consisting of cyclohexane, cyclohexanone, cyclohexanol, cyclohexylhydroperoxide, and a mixture thereof, the monobasic acid solvent comprises acetic acid, and the dibasic acid comprises adipic acid.

32. A method as defined in claim 28 wherein the hydrocarbon comprises a compound selected from a group consisting of cyclohexane, cyclohexanone, cyclohexanol, cyclohexylhydroperoxide, and a mixture thereof, the monobasic acid solvent comprises acetic acid, and the dibasic acid comprises adipic acid.

33. A method as defined in claim 29 wherein the hydrocarbon comprises cyclohexane, the monobasic acid solvent comprises acetic acid, and the dibasic acid comprises adipic acid.

34. A method as defined in claim 30 wherein the hydrocarbon comprises cyclohexane, the monobasic acid solvent comprises acetic acid, and the dibasic acid comprises adipic acid.

35. A method as defined in claim 31 wherein the hydrocarbon comprises cyclohexane, the monobasic acid solvent comprises acetic acid, and the dibasic acid comprises adipic acid.

36. A method as defined in claim 32 wherein the hydrocarbon comprises cyclohexane, the monobasic acid solvent comprises acetic acid, and the dibasic acid comprises adipic acid.

37. A method as defined in claim 25 wherein the step of reducing the Co in step (j) is performed by using acetaldehyde in an inert environment.

38. A method as defined in claim 25 wherein the step of reducing the Co in step (j) is performed by using a hydrocarbon in an inert environment.

39. A method as defined in claim 25 wherein the step (h) of oxidizing the Co is induced by using acetaldehyde in an oxidative environment.

40. A method as defined in claim 26 wherein the step of reducing the Co in step (j) is performed by using acetaldehyde in an inert environment.

41. A method as defined in claim 26 wherein the step of reducing the Co in step (j) is performed by using a hydrocarbon in an inert environment.

42. A method as defined in claim 26 wherein the step (h) of oxidizing the Co is induced by using acetaldehyde in an oxidative environment.

43. A method as defined in claim 27 wherein the step of reducing the Co in step (j) is performed by using acetaldehyde in an inert environment.

44. A method as defined in claim 27 wherein the step of reducing the Co in step (j) is performed by using a hydrocarbon in an inert environment.

45. A method as defined in claim 27 wherein the step (h) of oxidizing the Co is induced by using acetaldehyde in an oxidative environment.

46. A method as defined in claim 28 wherein the step of reducing the Co in step (j) is performed by using acetaldehyde in an inert environment.

47. A method as defined in claim 28 wherein the step of reducing the Co in step (j) is performed by using a hydrocarbon in an inert environment.

48. A method as defined in claim 28 wherein the step (h) of oxidizing the Co is induced by using acetaldehyde in an oxidative environment.

49. A method of preparing a dibasic acid by oxidizing a hydrocarbon, the oxidizing of the hydrocarbon comprising a step of separating a Co catalyst, used for promoting oxidizing of the hydrocarbon to the dibasic acid, by a process comprising the sub-steps of:
  (o) oxidizing substantially all Co to valence state 3 in the reaction mixture;
  (p) removing substantially all water;
  (q) reducing substantially all Co to valence state 2;
  (r) thermally precipitating the Co to form a catalyst precipitate;
  (s) separating the catalyst precipitate from the reaction mixture;
  (t) forming a solution of the separated catalyst; and
  (u) recycling the solution of the catalyst to any stage during or before the oxidation of the hydrocarbon.

50. A method as defined in claim 49 wherein step (o) of oxidizing the Co is preceded by a step of at least partially removing the dibasic acid.

51. A method as defined in claim 49 further comprising a step of re-oxidizing the Co substantially or predominantly to valence 3 between steps (t) and (u).

52. A method as defined in claim 50 further comprising a step of re-oxidizing the Co substantially or predominantly to valence 3 between steps (t) and (u).

53. A method as defined in claim 49 wherein the hydrocarbon comprises a compound selected from a group consisting of cyclohexane, cyclohexanone, cyclohexanol, cyclohexylhydroperoxide, and a mixture thereof, the monobasic acid solvent comprises acetic acid, and the dibasic acid comprises adipic acid.

54. A method as defined in claim 50 wherein the hydrocarbon comprises a compound selected from a group consisting of cyclohexane, cyclohexanone, cyclohexanol, cyclohexylhydroperoxide, and a mixture thereof, the monobasic acid solvent comprises acetic acid, and the dibasic acid comprises adipic acid.

55. A method as defined in claim 51 wherein the hydrocarbon comprises a compound selected from a group consisting of cyclohexane, cyclohexanone, cyclohexanol, cyclohexylhydroperoxide, and a mixture thereof, the monobasic acid solvent comprises acetic acid, and the dibasic acid comprises adipic acid.

56. A method as defined in claim 52 wherein the hydrocarbon comprises a compound selected from a group consisting of cyclohexane, cyclohexanone, cyclohexanol, cyclohexylhydroperoxide, and a mixture thereof, the monobasic acid solvent comprises acetic acid, and the dibasic acid comprises adipic acid.

57. A method as defined in claim 53 wherein the hydrocarbon comprises cyclohexane, the monobasic acid solvent comprises acetic acid, and the dibasic acid comprises adipic acid.

58. A method as defined in claim 54 wherein the hydrocarbon comprises cyclohexane, the monobasic acid solvent comprises acetic acid, and the dibasic acid comprises adipic acid.

59. A method as defined in claim 55 wherein the hydrocarbon comprises cyclohexane, the monobasic acid solvent comprises acetic acid, and the dibasic acid comprises adipic acid.

60. A method as defined in claim 56 wherein the hydrocarbon comprises cyclohexane, the monobasic acid solvent comprises acetic acid, and the dibasic acid comprises adipic acid.

61. A method as defined in claim 49 wherein the step of reducing the Co in step (q) is performed by using acetaldehyde in an inert environment.

62. A method as defined in claim 49 wherein the step of reducing the Co in step (q) is performed by using a hydrocarbon in an inert environment.

63. A method as defined in claim 49 wherein the step (o) of oxidizing the Co is induced by using acetaldehyde in an oxidative environment.

64. A method as defined in claim 50 wherein the step of reducing the Co in step (q) is performed by using acetaldehyde in an inert environment.

65. A method as defined in claim 50 wherein the step of reducing the Co in step (q) is performed by using a hydrocarbon in an inert environment.

66. A method as defined in claim 50 wherein the step (o) of oxidizing the Co is induced by using acetaldehyde in an oxidative environment.

67. A method as defined in claim 51 wherein the step of reducing the Co in step (q) is performed by using acetaldehyde in an inert environment.

68. A method as defined in claim 51 wherein the step of reducing the Co in step (q) is performed by using a hydrocarbon in an inert environment.

69. A method as defined in claim 51 wherein the step (o) of oxidizing the Co is induced by using acetaldehyde in an oxidative environment.

70. A method as defined in claim 52 wherein the step of reducing the Co in step (q) is performed by using acetaldehyde in an inert environment.

71. A method as defined in claim 53 wherein the step of reducing the Co in step (q) is performed by using a hydrocarbon in an inert environment.

72. A method as defined in claim 53 wherein the step (o) of oxidizing the Co is induced by using acetaldehyde in an oxidative environment.

* * * * *

UNITED STATES PATENT AND TRADEMARK OFFICE
CERTIFICATE OF CORRECTION

PATENT NO. : 6,326,455 B2
DATED : December 4, 2001
INVENTOR(S) : Eustathios Vassiliou et al.

It is certified that error appears in the above-identified patent and that said Letters Patent is hereby corrected as shown below:

Column 15,
Line 46, "(1) separating the catalyst precipitate," should read -- (1) separating the catalyst precipitate --.

Column 18,
Line 45, "A method as defined in claim 53," should read -- A method as defined in claim 52 --.
Line 48, "A method as defined in claim 53," should read -- A method as defined in claim 52 --.

Signed and Sealed this

Seventeenth Day of September, 2002

Attest:

JAMES E. ROGAN
Attesting Officer    Director of the United States Patent and Trademark Office